United States Patent [19]

Matthijsse

[11] 4,296,906
[45] Oct. 27, 1981

[54] DEVICE HAVING A BALANCED PIVOTABLE ARM

[75] Inventor: Matthijs Matthijsse, Eindhoven, Netherlands

[73] Assignee: U.S. Philips Corporation, New York, N.Y.

[21] Appl. No.: 77,423

[22] Filed: Sep. 20, 1979

[30] Foreign Application Priority Data

Sep. 29, 1978 [NL] Netherlands ............... 7809850

[51] Int. Cl.³ ............................................. E04G 3/00
[52] U.S. Cl. ................................. 248/280.1; 248/364; 248/584
[58] Field of Search ............ 248/571, 280.1, 564, 248/583, 584, 593, 595, 123.1, 325, 364

[56] References Cited

U.S. PATENT DOCUMENTS

| 684,167 | 10/1901 | Baker | 248/364 X |
| 2,584,921 | 2/1952 | Rainnsley et al. | 248/584 X |
| 2,665,102 | 1/1954 | Perbal | 248/584 |

FOREIGN PATENT DOCUMENTS

| 2448650 | 4/1975 | Fed. Rep. of Germany | 248/583 |
| 1038107 | 9/1953 | France | 248/584 |

*Primary Examiner*—J. Franklin Foss
*Attorney, Agent, or Firm*—Thomas A. Briody; Robert T. Mayer; Jack E. Haken

[57] ABSTRACT

A device having an arm which is pivotable around a first axle in a first plane of motion and is counterbalanced by means of a counterweight and wherein the first plane of motion is pivotable around a second axle which is perpendicular to the first axle. In order to permit the use of only one counterweight the counterweight is so coupled to the arm that, on pivoting of the arm, it moves along a straight line located in the first plane of motion, the counterweight and the center of gravity of the arm being on different sides of the second axle.

4 Claims, 2 Drawing Figures

DEVICE HAVING A BALANCED PIVOTABLE ARM

The invention relates to a device having at least one arm which is pivotable around a first axle in a first plane of motion and is counterbalanced by means of a counterweight, the first plane of motion being pivotable around a second axle which is perpendicular to the first axle and situated in the first plane of motion.

Such devices are, for example, used when an object must be scanned in accordance with a complicated pattern, as with an apparatus for medical examination by means of ultrasound (see the United States Patent Specification No. 3,924,452). The counterweight is required when the weight attached to the free end of the arm is heavy or when the arm is long. If, however, as customary, the counterweight is provided at the end of an extension of the arm, which extends to beyond the first axle it is often necessary to provide a second counterweight to prevent the device from being brought out of balance when the plane of motion is swung from the vertical position. Then the second counterweight must be located in the plane of motion at the side, located opposite the arm and the first counterweight, of the second axle. As a consequence the whole device becomes comparatively heavy, expensive and difficult to handle.

It is an object of the invention to provide a device which does not require a second counterweight. The device according to the invention is therefore characterized in that the counterweight is coupled to the arm via a transmission which is arranged so that the counterweight moves, on pivoting of the arm, along an approximately straight line situated in the first plane of motion, the counterweight and the centre of gravity of the arm being on different sides of the second axle.

Owing to these measures the arm is balanced by means of the first counterweight, both when it pivots around the first axle and when the plane of motion pivots around the second axle.

A preferred embodiment of the device according to the invention is characterized in that the transmission comprises:
a first connecting rod which is pivotable in a second plane of motion around a point of rotation and is coupled to the arm so that, when the arm pivots over a certain angle, it pivots over the same angle, there being a third axle which is perpendicular to the second plane of motion at the free end of this rod;
a first disc which is pivotable around the third axle and coupled so to a rigidly arranged second disc which is concentric to the point of rotation that, when the first connecting rod pivots over a certain angle, it rotates into the opposite direction over an angle which is twice as large;
a second connecting rod which is rigidly connected to the first disc and extends into the radial direction with respect to the first disc so that it encloses an acute angle with the first connecting rod when the angle between the arm and the second axle is smaller than 45°, the second connecting rod carrying the counterweight at its free end.

The first connecting rod can be coupled in a simple and cheap manner to the arm by means of a rope transmission or a chain transmission, A particularly compact construction of the device according to the invention is characterized in that the second plane of motion is perpendicular to the second axle.

The invention will be further explained with reference to the drawing in which

Figure 1:
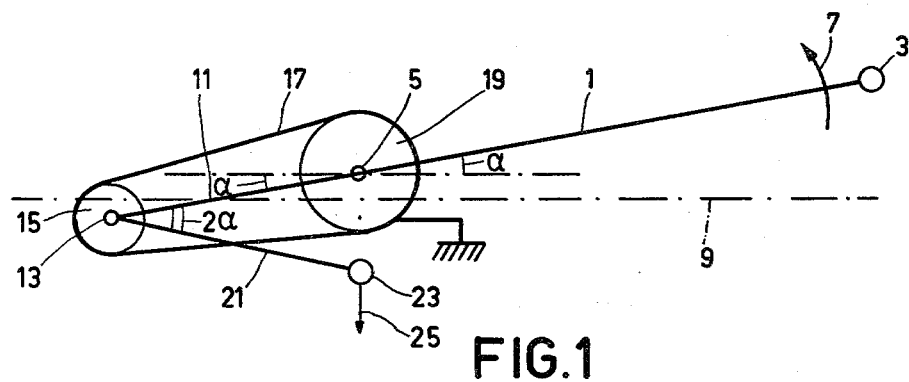
FIG. 1 is a schematic illustration of the principle of the invention.

FIG. 1 shows an arm 1 the weight of which is assumed to be concentrated in a point mass 3 and which is pivotable around a first axle 5 as indicated by the arrow 7. The arm 1 then moves in a first plane of motion which, in the position shown in the drawing, coincides with the plane of the drawing and which itself is pivotable around a second axle 9 (denoted by means of a dot-dash line) which is perpendicular to the first axle 5 and located in the first plane of motion. Beyond the first axle 5 the arm 1 is extended by means of a first connecting rod 11 which, on pivoting of the arm over an angle $\alpha$ pivots over the same angle $\alpha$ around a point of rotation which in this case coincides with the first axle 5. The first connecting rod 11 then moves in a second plane of motion which in this case of course coincides with the first plane of motion. If the first connecting rod 11 is not formed by an extension of the arm 1 but is connected to that arm in a different manner as will be described hereinafter with reference to FIG. 2, the second plane of motion may be at an angle to the first plane of motion.

A third axle 13 which is perpendicular to the second plane of motion is present at the free end of the first connecting rod. Rotatable around this third axle is a first disc 15, which is coupled by means of a rope 17 to a fixed second disc 19 (which therefore cannot rotate around its axle) and which is concentric to the point of rotation (the first axle 5). The diameter of the second disc 19 is twice the diameter of the first disc 15, so that on pivoting of the first connecting rod 11 over an angle $\alpha$ the first disc rotates in the opposite sense over an angle $2\alpha$ which is twice as large. The same effect can of course be obtained by coupling the two discs to one another by means of another transmission, for example a gear transmission.

A second connecting rod 21 is rigidly connected to the first disc 15 and extends into the radial direction with respect to the disc, so that it encloses an acute angle with the first connecting rod 11 when the angle between the arm 1 and the second axle 9 is smaller than 45°. A counterweight 23 is present at the free end of the second connecting rod 21.

The described connecting rod and disc assembly forms a transmission which is arranged so that, on pivoting of the arm 1 into the direction indicated by the arrow 7, the counter weight 23 moves along an approximately straight line in accordance with the arrow 25. When the two connecting rods 11, 21 are equally long, this line intersects the two axles 5, 9 at a right angle.

Figure 2:
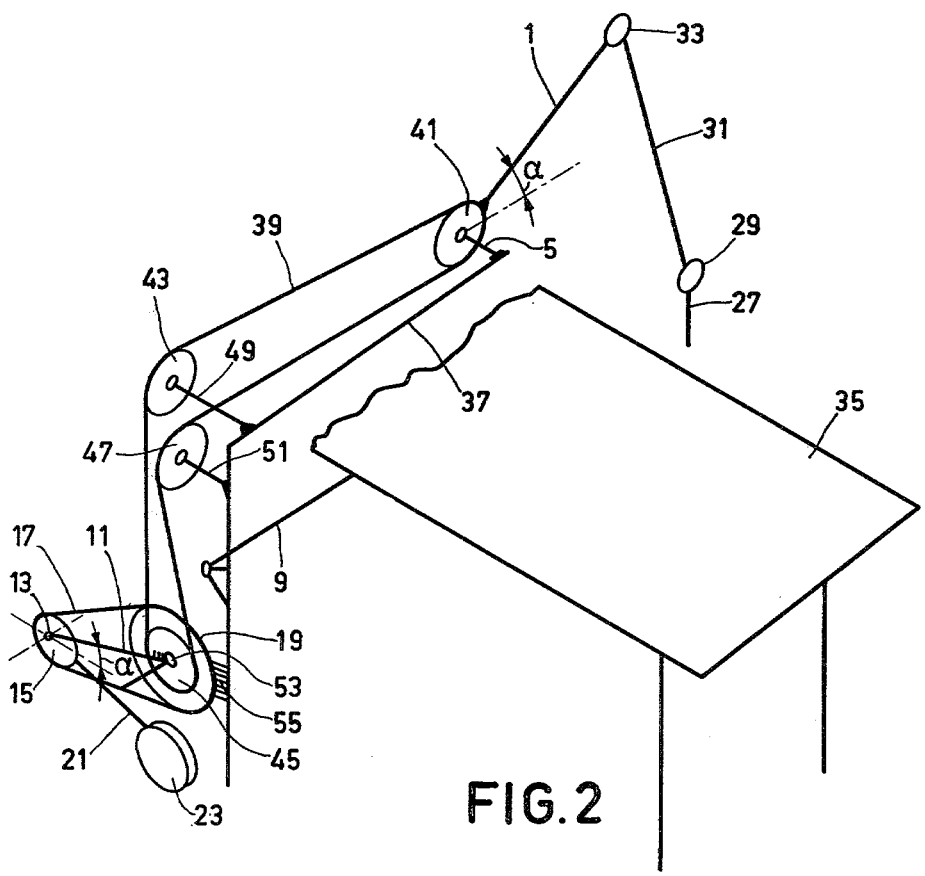
FIG. 2 shows a simplified representation of a preferred embodiment of a device according to the invention.

FIG. 2 shows schematically a practical embodiment of a device according to the invention wherein the principle explained with reference to FIG. 1 is used. Corresponding components are given the same reference numerals.

It relates to a device for medical examination of a patient by means of ultrasound waves which are transmitted and received by a transducer which is arranged in a measuring head 27. Via a hinge 29 this measuring head is connected to an intermediate arm 31, which in its turn is connected to the arm 1 by means of a hinge 33. During the examination the patient lies on a bed 35 and the measuring head 27 can be moved across his body, the position and the location of the measuring head being passed on to an electronic circuit, for example via potentiometers in the hinges. The electronic portion of the device is not important for an understanding of the invention and will therefore not be described here.

Via the first axle 5 the arm 1 is connected in a pivotable manner to a frame 37, which can pivot around the second axle 9, which is connected to the bed 35. If desired the second axle 9 may, of course, alternatively be connected to a stand which is separate from the bed 35.

This construction differs from FIG. 1 in that the arm 1 is coupled to the first connecting rod 11 by means of a rope transmission. This rope transmission is formed by a rope 39 which runs from a first rope wheel 41, which is rigidly connected to the arm 1 and is rotatable around the first axle 5, over a first guide wheel 43 to a second rope wheel 45 and back to the first rope wheel via a second guide wheel 47. The two guide wheels 43, 47 are rotatable around the auxiliary axles 49 and 51, respectively, which are in parallel with the first axle 5 and like this axle are connected to the frame 37. The second rope wheel 45 is rigidly connected to the first connecting rod 11 and, like this rod, is also rotatable around a point of rotation which in this case does, of course, not, coincide with the first axle 5. The rope transmission enables such a location of the axles 5 and 9 that all practical requirements imposed by the user on the device are satisfied and at the same time ensures that the counterweight 23 moves in the first plane of motion, the second axle 9 being between on the one hand the centre of gravity of the arm 1, inclusive of the components 27 to 31, inclusive, attached thereto and, on the other hand, the counterweight 23. Instead of a rope transmission it is, of course, alternatively possible to use an equivalent transmission, for example transmission by means of a chain.

The transmission between the second rope wheel 45 and the counterweight 23 is fully identical to the transmission in FIG. 1. The second disc 19 is rigidly connected to the frame 37 by means of a connecting piece 55 so that it cannot rotate around its axle. In order to limit the dimensions of the device in the first plane of motion, the transmission is arranged so that the second plane of motion is perpendicular to the second axle 9.

What is claimed is:
1. A counterbalancing device comprising:
a first axle (5);
an arm (1) pivotably affixed for rotation around the first axle in a first plane;
a second axle (9) disposed in the first plane perpendicular to the first axle;
means pivotably affixing the first axle and the arm for rotation around the second axle so that the center of gravity of the arm is disposed on a first side of the second axle;
a counterweight (23) disposed on a second side of the second axle opposite the center of gravity of the arm; and
transmission means which couple pivoting motion of the arm around the first axle to motion of the counterweight so that the counterweight moves in an approximately straight line in the first plane when the arm is rotated around the first axle.

2. A device as claimed in claim 1 wherein the transmission means comprise:
a first connecting rod (11) having a first end and a second end;
means coupling motion of the first connecting rod to motion of the arm so that when the arm is rotated through a given angle around the first axle the connecting rod rotates in a second plane of motion, through the same angle, about a point of rotation at its first end;
a third axle (13) disposed at the second end of the connecting rod and perpendicular to the second plane of motion;
a first disc (15) affixed for rotation around the third axle in the second plane of motion;
a second disc (19) disposed in the second plane of motion and having an axis at the point of rotation;
coupling means for coupling rotation of the first disc to rotation of the second disc so that when the first connecting rod pivots a given angle around the point of rotation the second disc rotates about that point through twice the given angle and in the opposite direction from the rotation of the connecting rod;
a second connecting rod (21), having a first end which is rigidly connected to the first disc, extending in the radial direction with respect thereto so that it encloses an acute angle with the first connecting rod when the angle between the first arm and the second axle is less than 45°, a second end of the second connecting rod supporting the counterweight.

3. A device as claimed in claim 2 wherein the means coupling motion of the first connecting rod to motion of the arm is a rope transmission or chain transmission.

4. A device as claimed in claim 3 wherein the second plane of motion is perpendicular to the second axle.

* * * * *